United States Patent [19]

Pero et al.

[11] Patent Number: 5,482,833
[45] Date of Patent: Jan. 9, 1996

[54] TEST TO DETERMINE PREDISPOSITION OR SUSCEPTIBILITY TO DNA ASSOCIATED DISEASES

[75] Inventors: Ronald W. Pero, New York; Daniel G. Miller, Scarsdale, both of N.Y.

[73] Assignee: Preventive Medicine Institute, New York, N.Y.

[21] Appl. No.: 430,326

[22] Filed: Apr. 26, 1995

Related U.S. Application Data

[63] Continuation of Ser. No. 869,823, Apr. 15, 1992, abandoned, which is a continuation of Ser. No. 333,841, Apr. 3, 1989, abandoned, which is a continuation of Ser. No. 820,203, Jan. 17, 1986, abandoned.

[51] Int. Cl.$^6$ .............................. C12Q 1/68; A61K 48/00; A61K 49/00
[52] U.S. Cl. ................... 435/6; 435/4; 435/15; 435/29; 435/173.1; 435/820; 436/501; 436/63; 436/64; 436/813; 436/815; 514/2; 514/44; 536/22.1; 536/25.3; 935/77
[58] Field of Search ............................. 435/4, 6, 15, 29, 435/173.1, 820; 436/501, 63, 64, 813, 815; 514/2, 44; 536/22.1, 25.3; 935/77

[56] References Cited

U.S. PATENT DOCUMENTS 4,585,736  4/1986  Dolbeare et al. ........................ 435/6

FOREIGN PATENT DOCUMENTS 3336786  3/1985  Germany ................................ 435/15

OTHER PUBLICATIONS

Pero et al. (1985) Carcinogenesis, vol. 6, No. 7, pp. 1055–1058.
Pero et al. (1985) Mutation Res., vol. 142, pp. 69–73.
Biological Abstracts 78 (7) 55503.
Biological Abstracts 80 (2) 13747.
Chemical Abstract 105: 19647.
Chemical Abstract 105: 95311.
Davis et al, Microbiology including Immunology and Molecular Genetics, 3rd ed., pp. 186–189 (1980).
Robbins, Pathologic Basis of Disease, pp. 148–152, (1974).
Simic et al, Mechanisms of DNA Damage and Repair, pp. 164–165 and 357–363, (1986).
Weisburger, J. "Bioassays and Tests for Chemical Carcinogens," Chemical Carcinogens, 1976, chapter 1, pp. 1–23.

*Primary Examiner*—W. Gary Jones
*Assistant Examiner*—Ardin H. Marschel
*Attorney, Agent, or Firm*—Cooper & Dunham

[57] ABSTRACT

Cellular DNA repair enzyme activity has been found to be an indicator of susceptibility or predisposition of an individual to DNA associated diseases. The activity of the enzyme adenosine diphosphate ribosyl transferase (ADPRT) has been found to be a good indicator as to the susceptibility of an individual to DNA associated diseases, such as cancer.

23 Claims, 1 Drawing Sheet

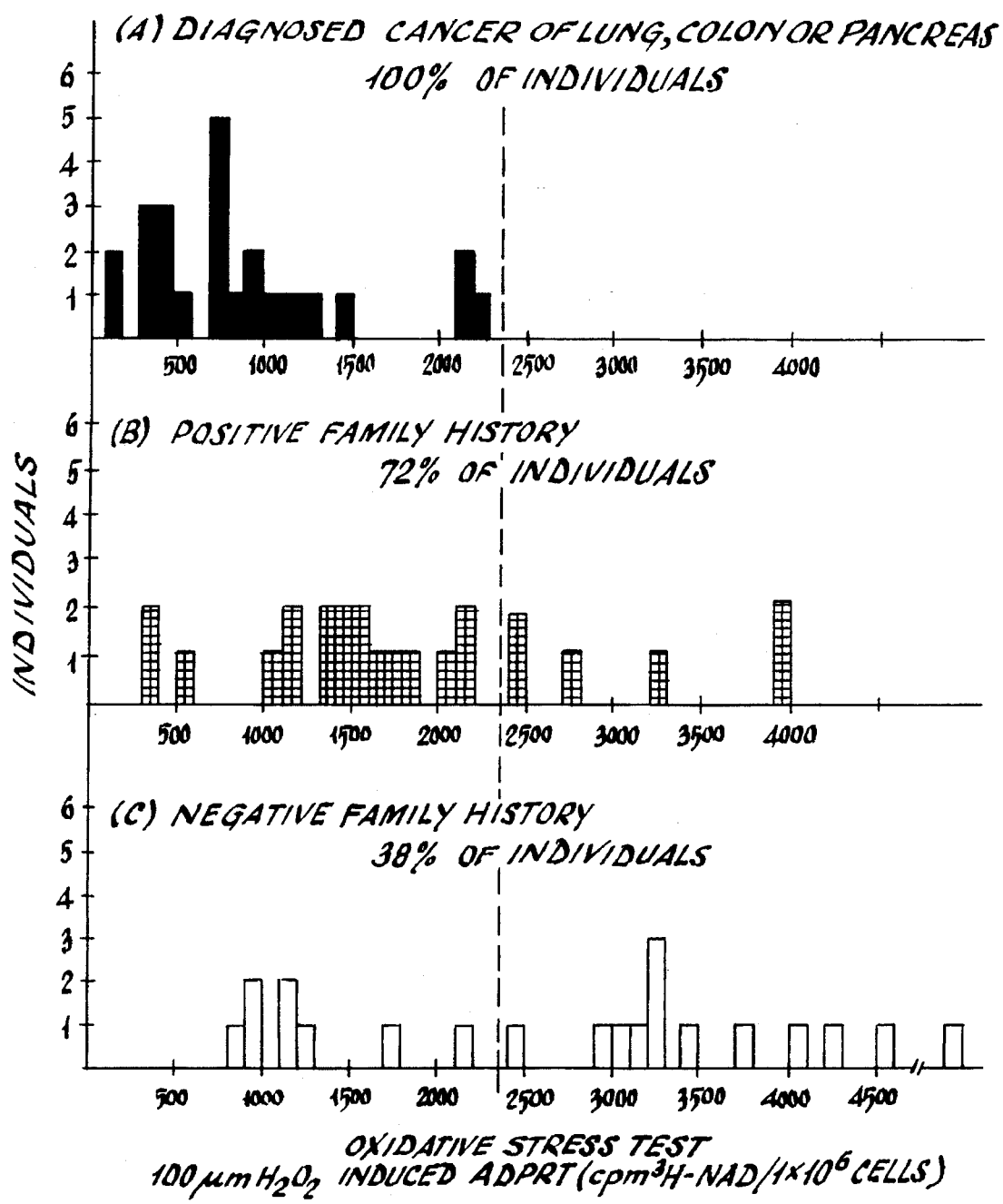

TEST TO DETERMINE PREDISPOSITION OR SUSCEPTIBILITY TO DNA ASSOCIATED DISEASES

This is a continuation of application Ser. No. 869,823 filed Apr. 15, 1992, which is a continuation of Ser. No. 333,841 filed Apr. 3, 1989, which is a continuation of application Ser. No. 820,203, filed Jan. 17, 1986 (all now abandoned).

BACKGROUND OF THE INVENTION

This invention relates to DNA associated diseases, such as cancer. In one aspect of this invention, this invention relates to a method for determining the level of cellular DNA repair enzyme activity. In another aspect, this invention relates to a method for monitoring the level of activity of cellular DNA repair enzymes in response to a stress. In another aspect, this invention relates to a method for screening individuals for the predisposition to cancer or other diseases associated with DNA damage. In yet another aspect, this invention relates to a method for screening therapeutic agents which may be useful for treating individuals with a predisposition to or a disease associated with DNA damage.

Most living cells possess systems for recognizing and eliminating DNA damage. As used herein, the term "DNA damage" refers to strand breaks, dimerization, unpaired bases, modified bases, conversion of one base into another resulting in unpaired bases, chromatin unwinding or other modifications, etc. For example, *E. coli* possesses a variety of enzymes for responding to DNA damage, such as enzymes of the SOS repair system and the various Rec proteins. These enzymes, and others, respond to DNA damage caused by U.V. radiation, chemical mutagens and the like. However, little is known about the mechanism by which the repair systems are activated by DNA damage.

In addition to the prokaryotic enzymes discussed above, eucaryotic and mammalian cells are also known to possess DNA repair enzymes. These enzymes are important in controlling diseases associated with DNA damage, as is clearly shown in the disease *Xeroderma pigmentosum* (Xp). This recessive disease results in hypersensitivity to sunlight, particularly to ultraviolet radiation. The disease is the result of a faulty excision repair system. Fibroblasts from Xp patients are deficient in the ability to excise and correct thymine dimers and other adducts. The deficit has been shown to be in enzymes that function at the excision step of repair. Another disease correlated with faulty DNA repair is Bloom's disease in which an increased frequency of chromosomal aberrations is seen.

DNA repair synthesis has been studied in cancer patients, see particularly the article by R. W. Pero et al entitled "Reduced Capacity for DNA Repair Synthesis in Patients with or Genetically Predisposed to Colorectal Cancer", *JNCI*, Vol. 70, No. 5, pp. 867–875, May, 1983, and the article by R. W. Pero et al entitled "Unscheduled DNA Synthesis in Mononuclear Leukocytes from Patients with Colorectal Polyps", *Cancer Research*, Vol. 45, pp. 3388–3391, July, 1985. These articles are of interest to the practices of this invention as applied to the measurement of the activity of DNA repair enzymes as being an indicator of the predisposition or susceptibility of an individual to colorectal cancer.

DNA damage, as indicated herein, may be caused by a number of agents. For example, oxygen supplied at concentrations greater than those of normal air has long been known to damage plants, animals and aerobic bacteria, see J. D. Ballantine, *Pathology of Oxygen Toxicity*, 1982, Academic Press, New York. It has been proposed that many of the damaging effects of $O_2$ could be attributed to the formation of $O_2$ radicals, see D. L. Gilbert (ed) *Oxygen and Living Processes: An Interdisciplinary Approach*, 1981, Springer Verlag, New York. The reactive oxygen species are superoxide, $H_2O_2$ and a hydroxyl radical. These are generated in vivo, i.e. endogenously in the body, as a consequence of normal metabolism, see B. N. Ames, *Science*, 221: 1256–1264, 1983. The oxidation of certain cellular components by these oxygen species could, in turn, contribute both to aging and to age-dependent diseases, such as cancer, see P. A. Cerutti, *Science*, 227:375–380, 1985.

$H_2O_2$ is produced by all viable cells, see Romasarma, *Biochem.Biophysica Acta*, 694:69–93, 1982, and it can be both a mutagen/carcinogen or promoter, see Troll & Wiesner, *Ann. Rev. Pharmocol. Toxicol.* 25:509–528, 1985, depending upon the cell type. The molecular response of a cell to stress whether it be induced by hyperthermia or by $H_2O_2$ is very similar, see Christman et al, *Cell* 41:753–762, 1985.

The practice of this invention in one embodiment employs $H_2O_2$ as an agent for oxidative stress to produce cellular DNA damage, thereby to induce a cellular DNA repair enzyme response, such as a response of the DNA repair enzyme adenosine diphosphate ribosyl transferase (ADPRT).

ADPRT is a nuclear enzyme which covalently attaches ADP-ribose moieties derived from NAD to chromatin proteins, see Hayoishi and Ueda, *Ann. Rev. Biochem.* 46:96–116, 1977 and Purnell et al *Biochem. Soc. Transa.* 8:215–227, 1980. The enzyme is dependent on DNA and is strongly stimulated by DNA-strand breaks, see Halldorsson et al *FEBS LETT.* 85:349–352, 1978; Benjamin and Pill. *J. Biol. Chem.* 255:10493–10508, 1980; Cohen and Berger, *Biochem. Biophys. Res. Commun.* 98:268–274, 1981. Although the role of ADPRT in cells is not fully understood, convincing data have been reported in its involvement in DNA repair, see Durkacz et al, *Nature* 283:593–596, 1980; Zwelling et al *Biochem. Biophys. Res. Commun.* 104:897–902, 1982; Althaus et al, *Biol. Chem.* 257:5528–5535, 1982; Chreissen and Shall, *Nature* 296:271–272, 1982 and Pero et al, *Chem. Biol. Interact.* 47:265–275, 1983. The involvement of this enzyme in cellular differentiation is reported by Farzaneh et al, *Nature* 300:262–266, 1982; Johnstone and Williams, *Nature* 300:368–370, 1982); and Pero et al *Carcinogensis* 6:1055–1058, 1985. The involvement of this enzyme in gene expression is mentioned by Althaus et al, *Nature* 300:366–368, 1982 and in connection with longevity by Pero et al, *Mutation Res.* 142:69–73, 1985. All these cellular events are important to the process of carcinogenesis and thus are important potential regulators of individual sensitivity or risk to develop cancer.

Although, as indicated herein, $H_2O_2$ has been known to be produced by viable cells and to have both carcinogenic and promoting properties, it has never been shown to directly activate ADPRT in eucaryotic cells. Moreover, interindividual variation in stress-induced ADPRT, such as oxidative, e.g. $H_2O_2$ stress-induced ADPRT, was not known nor was any link to cancer or DNA associated disease susceptibility previously known. In the development of this invention there has been observed in 100 uM $H_2O_2$-induced ADPRT measured values, a greater than 50-fold variation in the cell population tested.

The disclosures of the above-identified publications are herein incorporated and made part of this disclosure.

It is an object of this invention to provide a method whereby individuals with a predisposition to diseases associated with DNA damage could be recognized. Upon recognition, such individuals might then beneficially receive more frequent diagnostic examinations, pretreatment with drugs and the like.

It is also an object of this invention to provide a method for measuring the activity of DNA repair enzymes, particularly ADPRT activity.

It is also an object of this invention to provide a method for screening agents for potential therapeutic value for the treatment of individuals predisposed to diseases associated with the activity of DNA repair enzymes, such as the activity of ADPRT.

How these and other objects of this invention are achieved will become apparent in the light of the accompanying disclosure made with reference to the accompanying drawing which graphically illustrates the relationship of cancer patients and those with a positive family history of cancer or a negative family history of cancer with the measured ADPRT activity of such individuals.

SUMMARY OF THE INVENTION

In accordance with this invention a method has been developed to determine the predisposition or susceptibility of an individual to DNA associated disease. This method involves subjecting the cellular DNA of the individual to stress to induce or bring about DNA damage. The activity of the cellular DNA repair enzymes, particularly ADPRT activity, is then measured and the measured enzyme activity is then compared against a given or predetermined value to determine the relative predisposition or susceptibility of the tested individual to DNA associated disease, such as cancer. A measured value of cellular DNA repair activity, such as ADPRT activity, below said given value would indicate a greater susceptibility or predisposition to DNA associated diseases compared to an individual having a measured value above said given value.

BRIEF DESCRIPTION OF THE DRAWING

The Figure illustrates patient or family history relationships of cancer to measured ADPRT activity.

Section (A) of the Figure is a graph illustrating the relationship of cancer patients with the measured ADPRT activity of such individuals;

Section (B) of the Figure is a graph illustrating the relationship of persons with a positive family history of cancer with the measured ADPRT activity of such individuals; and Section (C) of the Figure is a graph illustrating the relationship of persons with a negative family history of cancer with the measured ADPRT activity of such individuals.

DETAILED DESCRIPTION OF THE INVENTION

The method of this invention for identifying an individual with a predisposition or susceptibility to diseases associated with the activity of DNA repair enzymes comprises isolating a cell, such as a mononuclear leukocyte or an epithelial or a fibroblast cell from the individual to be tested, stressing the cell to damage the cellular DNA structure to produce a stressed cell containing damaged cellular DNA and then determining a value for the ADPRT activity in the stressed cell. The measured value of ADPRT is then compared to the value of ADPRT activity in a cell from a so-called normal individual or a given value of ADPRT activity. A significant decrease in the activity of the enzyme ADPRT in the stressed cell would indicate a predisposition of the individual from whom such cells were taken and tested to DNA associated disease, such as cancer, relative to another individual whose cells, when so tested, show a higher measured DNA repair enzyme activity, such as ADPRT activity.

A variety of agents associated with causing DNA structural damage may be used in the practice of this invention to stress the cell to be tested to induce DNA damage. Those agents which cause oxidative stress are preferred, such as hydrogen peroxide, cumene hydroperoxide and benzoyl peroxide. Other agents usefully employed include xanthine, xanthine-oxidase, phorbol diesters and bleomycin. Radiation, such as ultraviolet radiation, gamma radiation or x-ray radiation, may also be employed to induce cellular DNA damage.

As indicated hereinabove, in the practices of this invention as an indicator of DNA repair enzyme activity, it is preferred to measure the value of ADPRT activity in a cell containing damaged DNA. In the preferred practice of this invention the activity of ADPRT is measured as counts per minute (cpm) of $^3$H-NAD per $1\times 10^6$. The cells to be tested, as indicated herein, could be isolated from a variety of tissues. Presently preferred cells for testing in accordance with the practice of this invention are the mononuclear leukocytes, fibroblasts or epithelial cells but other DNA containing cells may also be employed. The activity of ADPRT in the cell is determined by contacting the cell with hydrogen peroxide to produce a stressed cell containing damaged DNA, followed by measuring the activity of the ADPRT in the stressed cell to obtain a value for ADPRT activity. The value so obtained is compared with a predetermined value of at least about 1200 cpm $^3$H-NAD per $1\times 10^6$ cells, such as a value in the range 3500–4500 cpm $^3$H-NAD per $1\times 10^6$ cells. A significant difference of the measured value from the predetermined value would indicate that the cell so tested provides a modified cellular ADPRT activity.

In another embodiment of the practice of this invention there is presented a method for screening therapeutic agents for the treatment of individuals predisposed to diseases associated with DNA or the activity of DNA repair enzymes. The method comprises isolating a cell from a predisposed individual, stressing the cell with an agent to produce cellular DNA damage and with a therapeutic agent to produce a resulting stressed and treated cell. The activity of the DNA repair enzymes, such as ADPRT activity in the stressed and treated cell, is then determined to obtain a value of ADPRT activity and this value is compared against a predetermined value or a value obtained from a stressed cell which has not been treated with said therapeutic agent. If the ADPRT activity value of the stressed but untreated cell is less than the ADPRT value of the stressed and treated cell, this result would indicate that the tested therapeutic agent may be effective for the treatment of the predisposed individual.

The following is an example illustrative of the practice of this invention:

EXAMPLE

ADPRT is the only known biological reactant that consumes the ADP moiety of NAD. Accordingly, if NAD is radiolabeled in the adenine moiety, the trichloracetic acid (TCA)-precipitable radioactive counts would reflect ADPRT activity via (ADP-ribose)$_n$ polymerization to chromatin proteins. The protocol used to measure ADPRT activity is a modification of the procedure of Berger (D. M. Prescott ed), *Methods in Cell Biology* 20:325–400, 1978 and is published in detail by Pero et al in *Chem Biol Interactions* 147, 265–275, 1983.

ADPRT activity was measured as follows: Peripheral blood samples (20 ml) were collected by venous puncture into heparinized tubes (10–20 USP units/ml) from 24 individuals with diagnosed cancer of the lung, colon or pancreas, from 25 individuals with at least a first degree relative having either lung, colon or pancreas cancer and from 21 individuals with no family history of cancer. The mononuclear leukocyte fraction was isolated from the whole blood samples by density gradient centrifugation at 400×G for 20 minutes after layering on top of an Isopaque Ficoll cushion at a density of 1.077 gm/ml.

Duplicate cultures of $1-5 \times 10^6$ cells were incubated with or without either a standardized dose of either 100 uM $H_2O_2$ in 1.0% autologous plasma supplmented physiological saline for 60 minutes at 37° C. The resulting mixtures were removed at the end of the incubation period by centrifugation. The cells (+) and (−) $H_2O_2$ treatment were permeabilized, adjusted to $0.5 \times 10^6$ cells per treatment and ADPRT activity estimated after 15 minutes at 30° C. in a reaction mixture containing 175 uM (161.6 uCi/mmol) of [$^3$H] adenine-labeled NAD. The data were recorded as TCA precipitable [$^3$H]-NAD per $1 \times 10^6$ cells which were collected onto nitrocellulose filters. The (−) $H_2O_2$ ADPRT values were then subtracted from the (+) $H_2O_2$ values.

The results of these tests are graphically indicated in the accompanying drawing. As shown in the drawing, it can be seen that the frequency distribution of individual values for 100 uM $H_2O_2$ induced ADPRT varied in accordance with either the occurrence or the genetic predisposition to develop cancer. For example, when 100% of the values for the cancer patients were below ADPRT values of 2300, 72% of the individuals with a positive family history of cancer were below 2300 while the corresponding value for the group with no family history of cancer was 38%, all as indicated in the accompanying drawing. These results, as shown and quantified in the drawing, can usefully predict an individual's risk or predisposition or susceptibility to DNA associated disease, such as cancer.

Although in the practices of this invention it is preferred to measure directly ADPRT activity by the technique disclosed in the Example described hereinabove involving the measurement of TCA precipitated radiolabeled protein, the measurement of ADPRT activity can also be carried out indirectly through its effect or influence upon other DNA repair enzymes, such as topoisomerase, ligase and endonuclease and other related DNA associated enzymes, such as polymerase and exonuclease. The activities of these enzymes as affected by the activity of ADPRT can be separately measured by suitable techniques involving, as may be appropriate, radiolabeled components or monoclonal antibodies to components or products of the activity of such enzymes, particularly as may be influenced or effected by the activity of ADPRT.

As will be apparent to those skilled in the art in the light of the foregoing disclosure, many modifications, alterations and substitutions are possible in the practices of this invention without departing from the spirit or scope thereof.

What is claimed is:

1. A method for identifying an individual with a predisposition to diseases associated with the activity of DNA repair enzymes which comprises stressing cells of said individual to produce stressed cells containing damaged DNA, thereby to cause induced activity of adenosine diphosphate ribosyl transferase (ADPRT) in the stressed cells, determining a value for the induced activity of the ADPRT in the stressed cells, and comparing the value so determined with a reference value of the activity of ADPRT to ascertain whether said value so determined is higher or lower than said reference value, a determined value lower than said reference value identifying said individual as having said predisposition.

2. A method in accordance with claim 1 wherein the cell is subjected to stress by exposure to radiation.

3. A method in accordance with claim 1 wherein said cells are stressed by ultraviolet radiation.

4. A method in accordance with claim 1 wherein said cells are stressed by x-ray radiation.

5. A method in accordance with claim 1 wherein the cells are subjected to oxidative stress.

6. A method in accordance with claim 5 wherein said oxidative stress involves exposure to hydrogen peroxide.

7. A method in accordance with claim 5 wherein said oxidative stress involves exposure to cumene hydroperoxide.

8. A method in accordance with claim 5 wherein said oxidative stress involves exposure to benzoyl peroxide.

9. A method in accordance with claim 5 wherein said oxidative stress involves exposure to xanthine-xanthine oxidase.

10. A method in accordance with claim 1 wherein the cells are subjected to stress by contact with phorbol esters.

11. A method in accordance with claim 1 wherein the cells are subjected to stress by contact with bleomycin.

12. A method in accordance with claim 1 wherein the activity of ADPRT is measured as cpm $^3$H-NAD per $1 \times 10^6$ cells.

13. A method in accordance with claim 1 wherein said cells are mononuclear leukocytes.

14. A method in accordance with claim 1 wherein said cells are fibroblasts.

15. A method in accordance with claim 1 wherein said cells are epithelial cells.

16. A method for screening therapeutic agents suitable for the treatment of individuals predisposed to diseases associated with DNA which comprises stressing cells of an individual to produce DNA damage, thereby to cause induced activity of adenosine diphosphate ribosyl transferase (ADPRT) in the stressed cells, contacting or treating the resulting stressed cells with a therapeutic agent to produce resulting stressed and treated cells, determining a value for the induced activity of the ADPRT in the resulting stressed and treated cells, and comparing the value so determined with a predetermined value to evaluate the effectiveness of the therapeutic agent for the treatment of said individual by ascertaining whether said obtained value is higher or lower than said predetermined value, an obtained value higher than said predetermined value indicating that the therapeutic agent is effective for the treatment of said individual.

17. A method of testing an individual for a predisposition to a disease associated with DNA damage, comprising stressing DNA-containing cells of the individual to produce stressed cells having damaged cellular DNA, thereby to cause induced activity of adenosine diphosphate ribosyl transferase (ADPRT) in the stressed cells, determining a value for the induced activity of ADPRT in the stressed cells, and comparing the value so determined with a reference value of ADPRT activity to ascertain whether said value so determined is higher or lower than said reference value, wherein said predisposition is indicated if said value so determined is lower than said reference value.

18. A method according to claim 17, wherein said cells are mononuclear leukocytes, epithelial cells, or fibroblast cells.

19. A method according to claim 18, wherein said cells are mononuclear leukocytes.

20. A method according to claim 17, wherein said disease is cancer.

21. A method according to claim 20, wherein said disease is cancer of the colon, liver or pancreas.

22. A method for testing the immune competency of an individual, comprising stressing DNA-containing cells of the individual to produce stressed cells having damaged cellular DNA, thereby to cause induced activity of adenosine diphosphate ribosyl transferase (ADPRT) in the stressed cells, determining a value for the induced activity of ADPRT in the stressed cells, and comparing the value so determined with a reference value of ADPRT activity to ascertain whether said value so determined is higher or lower than said reference value, wherein a low immune competency with respect to a disease associated with cellular DNA damage is indicated if said value so determined is lower than said reference value.

23. A method for testing the efficacy of a therapeutic agent for treating an individual for a disease associated with DNA damage, comprising stressing DNA-containing cells of the individual to produce stressed cells having damaged cellular DNA, thereby to cause induced activity of adenosine diphosphate ribosyl transferase (ADPRT) in the stressed cells, determining a value for the induced activity of ADPRT in the stressed cells, and comparing the value so determined with a reference value of ADPRT activity to ascertain whether said value so determined is higher or lower than said reference value, wherein said cells are cells treated with said agent, and wherein efficacy of said agent is indicated when said determined value is higher than said reference value.

\* \* \* \* \*